(12) United States Patent
Kai (10) Patent No.: US 7,601,125 B1
(45) Date of Patent: Oct. 13, 2009

(54) SURGICAL, GROOVED DIRECTOR FOR COLLECTING TISSUE IN A MINIMALLY INVASIVE MANNER

(76) Inventor: Desinger Kai, Rubensstr. 108, Berlin (DE) D-12157

( * ) Notice: Subject to any disclaimer, the term of this patent is extended or adjusted under 35 U.S.C. 154(b) by 0 days.

(21) Appl. No.: 10/018,154

(22) PCT Filed: Apr. 8, 2000

(86) PCT No.: PCT/EP00/03146

§ 371 (c)(1),
(2), (4) Date: Mar. 29, 2002

(87) PCT Pub. No.: WO00/78221

PCT Pub. Date: Dec. 28, 2000

(30) Foreign Application Priority Data

Jun. 17, 1999 (DE) ................................ 199 27 650

(51) Int. Cl.
*A61B 10/00* (2006.01)
(52) U.S. Cl. .................. 600/564; 600/567; 606/167
(58) Field of Classification Search ............... 600/562, 600/564–567; 606/45–50, 167, 170, 174
See application file for complete search history.

(56) References Cited

U.S. PATENT DOCUMENTS

| 5,649,547 A | * | 7/1997 | Ritchart et al. ............... 600/566 |
| 5,775,333 A | | 7/1998 | Burbank |
| 5,782,795 A | | 7/1998 | Bays |
| 5,810,806 A | | 9/1998 | Ritchart |
| 5,817,034 A | | 10/1998 | Milliman |
| 6,331,166 B1 | * | 12/2001 | Burbank et al. ............. 600/567 |
| 6,454,727 B1 | * | 9/2002 | Burbank et al. ............. 600/567 |
| 6,699,206 B2 | * | 3/2004 | Burbank et al. ............. 600/567 |

FOREIGN PATENT DOCUMENTS

| DE | 19528440 A1 | 2/1997 |
| DE | 19706751 A1 | 10/1997 |
| JP | 10043197 | 2/1998 |
| JP | 10216148 | 8/1998 |
| WO | WO 95/08291 | 3/1995 |
| WO | WO 99/44506 | 9/1999 |

* cited by examiner

*Primary Examiner*—Max Hindenburg
*Assistant Examiner*—Jonathan M Foreman
(74) *Attorney, Agent, or Firm*—Beck & Tysver PLLC (57) ABSTRACT

A surgical hollow probe for minimally invasive tissue removal comprising an elongate hollow body, an opening in the region of the distal end of the hollow body and an opening in the region of the proximal end of the hollow body for respectively receiving and delivering tissue, and comprising an electrically conductive ring-shaped or loop-shaped cutting element which can be extended from the hollow body and which can be applied to an HF-voltage source, for cutting out tissue in the area around the distal opening of the hollow body.

16 Claims, 9 Drawing Sheets

SURGICAL, GROOVED DIRECTOR FOR COLLECTING TISSUE IN A MINIMALLY INVASIVE MANNER

The invention concerns a surgical hollow probe for minimally invasive tissue removal comprising an elongate hollow body having an opening in the region of the distal end of the hollow body for receiving tissue and an electrically conductive ring-shaped or loop-shaped cutting element which can be extended from the hollow body and which can be connected to an HF-voltage source for electrosurgically cuffing out tissue in the area around the distal opening of the hollow body.

BACKGROUND OF THE INVENTION

In the context of minimally invasive medicine, the endeavour is to implement an operating procedure which causes the minimum trauma for the patient. In that respect, the endeavour is to go either by way of the natural body openings of the patient as in the case of interventional endoscopy or through small incisions to directly reach the point of engagement into the depths of the tissue in order to remove tissue for diagnostic purposes, for example for histological tissue determination, or for therapy procedures, or for removal of a tumour.

The development of corresponding instruments for minimally invasive surgery made rapid progress in recent years as this operational technique affords considerable advantages for cosmetic reasons, for minimising post-operative complications and for accelerating the healing process.

Apparatuses are known by the 'name fine needle aspiration' (FNA) or 'true cut needle biopsy', having a fine needle which is introduced into a suspicious area of tissue and by means of which one or more samples of tissue can be taken purely mechanically by way of a stamping mechanism in order to subject that tissue to histological examination.

Thereafter suitable surgical measures can possibly be initiated in the event of malignant findings. The volumes of tissue which can be removed with these known needle probes are however only very small and are therefore suitable exclusively for diagnostic purposes. By virtue of the small volume of tissue which can be taken in one insertion, a plurality of insertions into the suspicious area of tissue are accordingly often required, which under some circumstances can result in malignant tumour cells being spread thereby. In addition, the levels of accuracy of the histological tissue findings are not optimum because of the small volume of tissue sampled.

U.S. Pat. No. 5,775,333 or U.S. Pat. No. 5,782,795 disclose surgical Instruments which permit relatively large volumes of tissue to be removed by multiple tissue removal from the same target area. Those known instruments involve using a vacuum-aided mechanical stamping-cutting device which reduces the number of insertions required and which in addition—because of the larger volume of tissue removed—also improves the accuracy of the diagnostic results. Those known instruments can also often be used to remove in toto relatively small tissue changes, which under some circumstances makes a subsequent Operation unnecessary.

When using the Instrument disclosed in U.S. Pat. No. 5,775,333, a needle-shaped hollow probe is introduced into the target area, for example a breast tumour. Disposed laterally at the end of that probe is an elongate opening into which the tissue to be removed is sucked. Disposed within the device is a rotating hollow blade which, by way of a mechanical forward movement, cuts off the tissue which has been sucked into the opening, within the device, and sucks it by a vacuum through the hollow probe. By successively turning the shaft through 360°, a given volume of tissue which has been previously sucked into the hollow probe and cut off therein is thus removed around the distal end of the probe, which however is often not entirely sufficient for complete removal of the medically suspicious area of tissue.

U.S. Pat. No. 5,817,034 discloses a surgical Instrument in which a hollow cylindrical blade of a diameter of up to 25 mm is driven forward to the target area. By way of a loop which is disposed at the end and which is supplied with HF-voltage, the head portion of the cylinder which is thus stamped out within the device is severed and then the entire severed cylinder of tissue is removed by way of the device. With that known System, the suspicious area of tissue can admittedly be removed in toto, but a very large amount of healthy tissue is also removed, until the probe tip has reached the suspicious area of tissue, and a relatively large scar is left, due to the large diameter of the device.

U.S. Pat. No. 5,810,806 discloses a surgical probe in which the tissue is not cut by means of a mechanical ring-shaped blade but by means of an axially non-displaceable loop which is fixed to the distal end of the hollow body and which is supplied with an HF-voltage and thereby acts as a cutting blade. In a cutting procedure, the cylinder of tissue which is severed at the periphery by the HF-loop is displaced frontally into the frontally open hollow body and then at the end of the procedure it is cut off by a windshield-like rotary movement of the loop which is supplied with HF-voltage. In the case of this known device also the tissue is completely severed only when it is in the hollow body, whereby a great deal of healthy tissue is also removed up to the time that the tip of the probe has been advanced to the suspicious area of tissue. A further disadvantage is that only the cylinder of tissue in front of the front opening of the hollow body can be removed.

DE 197 06 751 or DE 195 28 440 disclose an electrosurgical implement of the kind set forth in the opening part of this specification, in which a loop-shaped cutting element for electrosurgically cutting out tissue is oriented in parallel relationship with the longitudinal axis of an elongate hollow body and, while maintaining that orientation, can be extended in a loop-shaped configuration from the hollow body so that then the adjoining tissue can be cut out in a toric configuration by virtue of rotary movement of the hollow probe. The tissue which has been cut out can then be passed into the hollow passage of the hollow body through the same opening through which the cutting element issues, and can then be transported along the hollow passage to the proximal end of the implement. That known implement enjoys the advantage that the point of insertion is of small dimensions and that it is then possible to remove at the point of treatment a portion of tissue which externally surrounds the hollow probe in adjoining relationship. A disadvantage in this case however is that the volume of tissue which can be cut out is relatively small and is therefore not sufficient for thoroughly examining even relatively large areas of tissue.

WO 99/44506 which is published after the relevant date discloses a loop-shaped cutting element which can be extended from the hollow body in a plane which extends transversely with respect to the longitudinal axis of the hollow body, wherein after extension of the cutting element the cutting element is displaceable along the hollow body.

SUMMARY OF THE INVENTION

The object of the invention is to develop the surgical probe of the kind set forth in the opening part of this specification with which, with an incision of a small diameter, it is possible to remove a comparatively larger and interconnected amount of tissue without substantial amounts of healthy tissue also having to be removed in that procedure.

In a surgical probe of the kind set forth in the opening part of this specification, that object is attained in accordance with the invention in that the cutting element can be extended from or pivoted out of the hollow body transversely with respect to the longitudinal axis of the hollow body and is then displaceable outside the hollow body in parallel relationship with the longitudinal axis of the hollow body.

The advantages of the invention are in particular that, after insertion of the hollow probe into the tissue, the cutting element can be extended radially from the hollow body and then—by means of intermittent rotary movement of the hollow probe about its longitudinal axis—it is possible to cut out a plurality of cylinders of tissue which are adjacent to the periphery of the hollow probe and which can then be transported for example by way of a suction device through the distal opening into the hollow body and then to the proximal opening of the hollow body.

For example it is possible to implement a first cut in perpendicular relationship to the hollow probe upon radial extension of the cutting blade, then to cut out the periphery of a first cylinder of tissue which is outside the hollow probe when the cutting element is displaced in the longitudinal direction of the hollow probe and finally to cut off the cylinder of tissue at its end when the hollow probe and therewith the cutting element is rotated about the longitudinal axis thereof through a predetermined rotary angle. Then, by again displacing the cutting element in parallel relationship to the longitudinal axis of the hollow probe, it is possible to cut away a further cylinder of tissue at its periphery and then also to cut it off—at its end—by again rotating the hollow probe.

In that way the hollow probe according to the invention makes it possible to cut out a ring of parallel cylinders of tissue, which adjoin the periphery of the hollow probe and which are oriented in parallel relationship with the longitudinal axis of the hollow probe. The amount of tissue which can be collected in that way is composed of a plurality of individual cylinders of tissue which each in itself is approximately of the volume which can be collected with the known surgical hollow probes (for example from U.S. Pat. No. 5,810,806). In that respect the diameter of the insertion puncture remains limited to the diameter of the hollow probe. The HF-voltage which is required for the cutting Operation and which is applied to the cutting element generates an HF-current which flows in known manner through the tissue to a counterpart electrode which for example is applied from the exterior to the skin of the patient or which is arranged on the hollow body of the hollow probe.

Preferably the ring-shaped or loop-shaped cutting element is extendable from the hollow body in a surface or plane which extends transversely with respect to the longitudinal axis of the hollow body and then—during a cutting operation, that is to say while the cutting element is moved along the path of displacement travel—it remains oriented perpendicularly with respect to the longitudinal axis. In that way—with a predetermined shape for the cutting element—it is possible to cut out the maximum volume of tissue in each cutting operation.

The distal opening preferably extends on the peripheral wall of the hollow body along the path of displacement travel of the cutting element so that, with a slight rotary movement of the hollow probe, the tissue which is cut away can then be easily transferred into the distal opening.

In accordance with a further preferred embodiment of the invention, the cutting element is in the form of a wire loop or wire sling or noose, the two ends of which are secured jointly to a thrust rod or each separately to a respective thrust rod, wherein the thrust rods are supported slidably in parallel relationship to the longitudinal axis of the hollow body in longitudinal grooves at the outside surface of the hollow body.

Alternatively, the cutting element is in the form of a closed wire ring which is fixed at its outside periphery to a guide element, for example a thrust rod which is guided slidably in a longitudinal groove along the hollow body. The cutting element comprises for example a flexible wire which can be moved easily out of and into the hollow body, for example through a slot in the peripheral wall of the hollow body.

The cutting element is connected to an HF-voltage source which is at the proximal end of the hollow probe, by way of a connecting line which is guided for example along the inside wall of the hollow body. The other terminal of the HF-voltage source is connected to a counterpart electrode which is either applied from the exterior to the skin of the patient or—in order to prevent uncontrolled flow of current through the tissue—is on the hollow body or is part of the hollow body. If the hollow body is made from metal, then the entire hollow body of the hollow probe can serve as the counterpart electrode, thereby affording a controlled, locally closely delimited flow of current from the cutting element to the counterpart electrode. They are then however both to be well electrically insulated from each other in order to avoid a short-circuit.

In accordance with a preferred embodiment of the invention, the distal opening is disposed in the distal region in the peripheral wall of the hollow body, adjacent the longitudinal grooves in which the thrust rods are longitudinally slidably guided.

Preferably the distal opening is delimited by wall edges which extend parallel to the longitudinal groove or grooves. The internal width of the distal opening is preferably greater in the axial direction than the maximum axial displacement travel so that the cylinders of tissue which are cut out can be easily conveyed through the distal opening into the hollow body and therein to the proximal end of the hollow probe. If the cutting element is in the form of a wire loop whose two ends are guided in two spaced longitudinal grooves on guide elements or thrust rods, then the distal opening can preferably be provided at the periphery of the hollow body between the two longitudinal grooves. The cylinder of tissue which is cut away can then be transported without rotation of the probe into the hollow space in the hollow body.

Alternatively, the cutting element may also be composed of a plurality of wire segments which are secured to thrust rods in mutually displaced relationship in the longitudinal direction of the hollow body, wherein the thrust rods are guided slidably in longitudinal grooves along the hollow body. In this embodiment of the invention, the wire segments are so shaped that their projection onto a plane perpendicular to the longitudinal axis, together with the peripheral wall of the hollow body, forms a closed curve, wherein all wire segments are connected to the one terminal of the HF-voltage source and the counterpart electrode can be, in conventional manner, the hollow body or a separate external counterpart electrode.

Preferably, at least one of the thrust rods, which are displaceable in the longitudinal grooves, is supported rotatably in the longitudinal groove in question. Provided at the distal end and/or at the proximal end of the displacement travel in the hollow body is a gap, in the peripheral direction, through which the cutting element extends from the hollow body when the thrust rod to which the cuffing element is secured is suitably rotated.

Preferably the distal opening of the hollow body is closable by means of a closure in order not to impede insertion of the probe into the tissue and in order to ensure, after the cylinder of tissue which has been cut out has been sucked in, that adjoining tissue which has not been cut away is not sucked into the opening when the cylinder of tissue is transported away by a vacuum effect to the proximal end. The closure is preferably displaceable in the radial and/or axial direction along the peripheral wall of the hollow body, for example the closure can be embodied in the form of a rotary sleeve which is mounted rotatably in the interior of the hollow body and which also has a distal opening which can be brought into register relationship with the distal opening of the hollow body.

So that tissue which has been cut out can be sucked into the distal opening, it is possible to connect to the hollow probe in proximal relationship therewith a suction removal device which in the longitudinal direction of the how probe contains a separate suction air passage which extends from the proximal connection to the distal opening of the hollow body and which is in suction communication with the hollow passage of the hollow body by way of suction openings.

In a particularly preferred feature, the distal end of the hollow probe converges to a point and carries a first electrode which can serve as the counterpart electrode for the cuffing element when cuffing out tissue. In the cutting mode for this embodiment, a terminal of the HF-voltage source is connected to the cutting element while the other terminal is connected to the first electrode. Upon insertion of the probe, the cutting element is disposed in the interior of the hollow body, without voltage being applied thereto. It is particularly preferable for the first electrode to be supplied with HF-voltage during the insertion procedure and for a counterpart electrode to be applied to the patient from the exterior in the proximity of the area of tissue to be investigated. The tissue adjoining the probe is then thermally inactivated over an individually predeterminable period of time by means of a locally limited, high-frequency alternating current. If, in addition, a second electrode is applied to the hollow body at a predetermined axial spacing, then the high-frequency alternating field can be produced between the two preferably cylindrical electrodes, whereby the alternating field-upon insertion of the probe—is limited locally to immediately adjoining areas of tissue. The counterpart electrode which is applied from the exterior can then be omitted. In that respect, the HF-voltage is so fixed that temperatures of between 55° and 10° C., preferably between 60° and 80° C., are maintained in the tissue over a relatively long period of between, for example, 5 and 20 minutes in order thus irreversibly to terminate metabolic procedures within the tumour cells. This thermal inactivation effect ensures that the tumour cells can no longer spread and metastasize in the subsequent tissue removal procedure.

In accordance with a further preferred embodiment of the invention, a plurality of cutting elements can be extended from the hollow body transversely with respect to the longitudinal axis of the hollow body and are then displaceable in the longitudinal direction outside the hollow body. Preferably, associated with each cuffing element is a distal opening at the peripheral wall of the hollow body, the opening extending along the path of displacement travel of the cutting elements in question.

BRIEF DESCRIPTION OF THE DRAWINGS

Advantageous developments of the invention are characterised by the features of the appendant Claims.

Embodiments of the invention are described in greater detail hereinafter with reference to the accompanying drawings in which.

DETAILED DESCRIPTION OF PREFERRED EMBODIMENT(S)

FIGS. 1 to 6 show various embodiments of a surgical hollow probe which serves for minimally invasive removal of tissue from a human or an animal organism. The hollow probe I includes a cylindrical hollow body 2 of a uniform circular cross-section, which at its distal end 4 has a tip 6 and which at its proximal end (not shown) includes various actuating devices for actuating the elements of the hollow probe and connections for the connection of supply sources, for example vacuum or suction devices 5 or an HF-voltage source 7.

The hollow body 2 has a central longitudinal axis 3 and an internal hollow passage 8 which extends from the distal region 4 to the proximal region of the hollow probe I and which forms a transportation path for pieces of tissue which are cut away in the area around the distal region and are to be transported to the proximal end of the hollow probe 1.

Provided on the peripheral surface of the hollow body 2 in parallel relationship to the longitudinal axis 3 of the hollow body 2 is a longitudinal groove 16 in which a guide element, for example a thrust rod 14, is longitudinally slidably mounted. The thrust rod 14 extends to the proximal end of the hollow body 2 and it can there be displaced by the operator by means of actuating devices (not shown). A cutting element 10 is fixed to the thrust rod 14, more specifically preferably in the distal region or at the distal end of the thrust rod 14. In the embodiment of the hollow probe I shown in FIGS. 1 to 4, the cutting element 10 is in the form of a rigid or flexible wire ring whose diameter is slightly smaller than the inside diameter of the hollow passage 8. The cutting element is slidable together with the thrust rod 14 along the hollow body 2, being disposed in each case in such movement in a plane which perpendicularly intersects the longitudinal axis 3, A gap 18 is formed in the peripheral wall of the hollow body 2 in the peripheral direction at the distal end of the longitudinal groove 16, that is to say at the distal end of the path of displacement travel of the cutting element 10. In addition to being displaceable, the thrust rod 14 is also mounted rotatably in the longitudinal groove 16 so that—upon reaching its distal end position—the cutting element 10, by rotary movement of the thrust rod 14, can be turned through the gap 18 into the hollow passage 8 of the hollow body 2 or, in that distal end position, the cutting element can be extended through the gap 18 from the hollow body 8.

Figure 1:
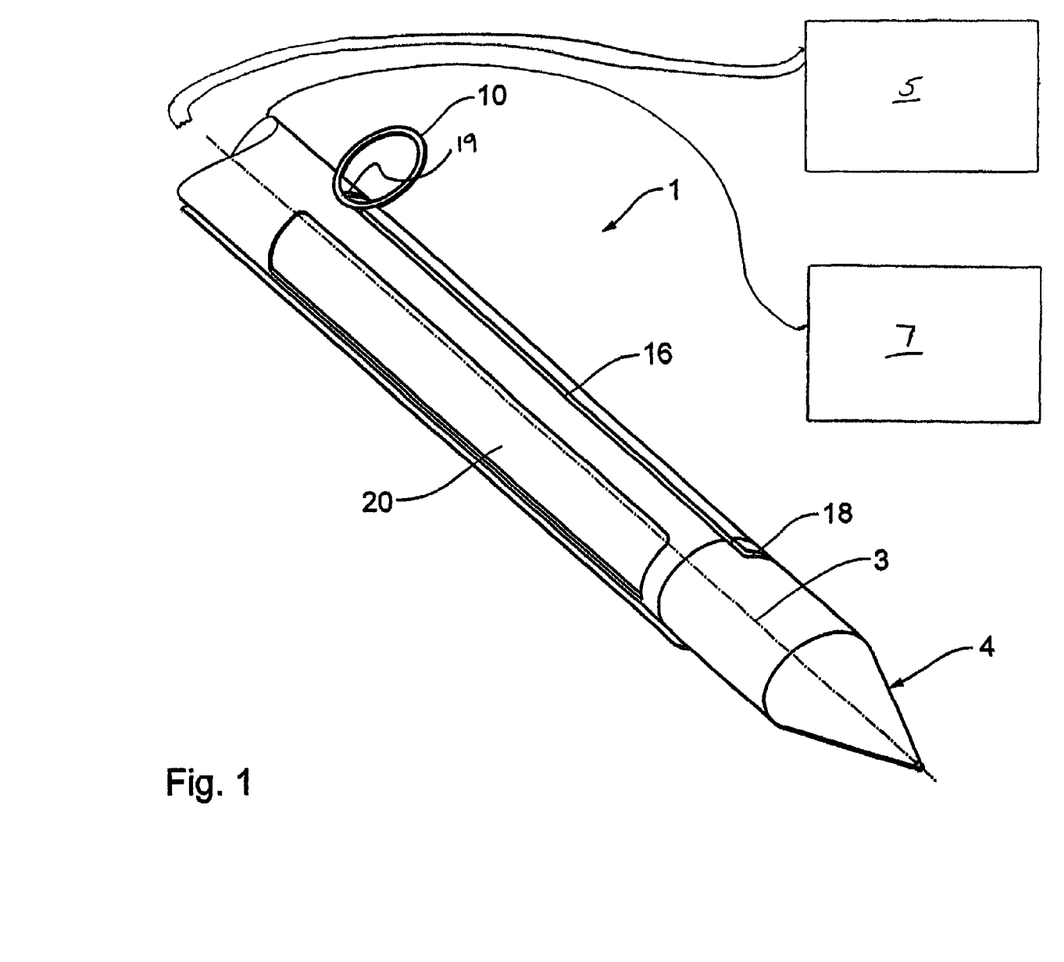
FIG. 1 is a perspective view of a first embodiment of a surgical hollow probe.

In the embodiment illustrated in FIG. 1, a gap 19 is formed in the peripheral wall of the hollow body 2 in the peripheral direction at the proximal end of the longitudinal groove 16, that is to say at the proximal end of the path of displacement travel of the cutting element 10.

Figure 2:
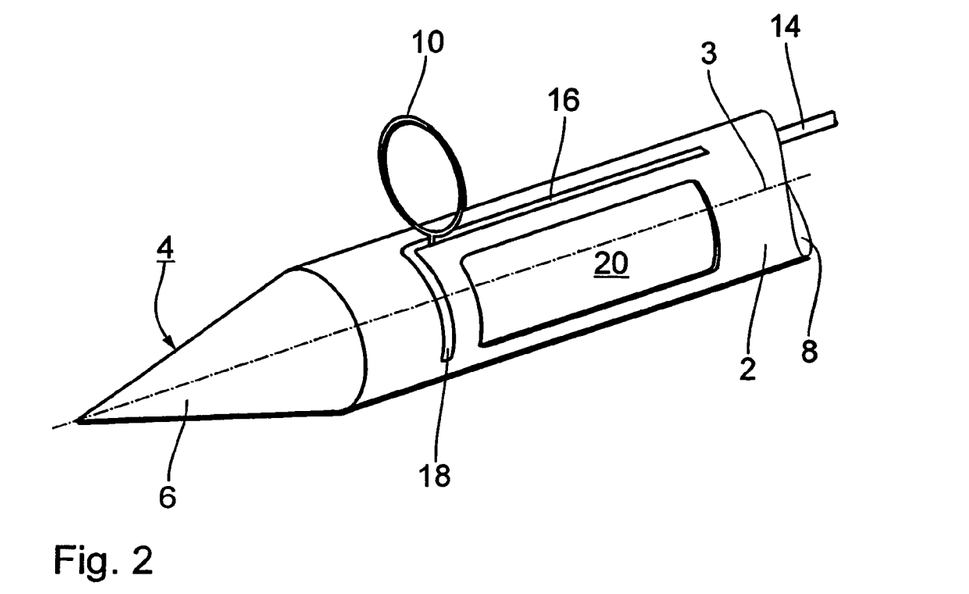
FIG. 2 is a view of part of the hollow probe shown in FIG. 1.

Provided in the distal region in the peripheral wall of the hollow body 2 is a distal opening 20 which extends along the path of displacement travel of the cutting element 10 and—in the illustrated embodiment—is defined by longitudinal edges which extend parallel to the longitudinal groove 16. In addition, in the illustrated embodiment, the distal opening 20 is defined by wall edges which extend parallel to the gap 18, that is to say in the peripheral direction, perpendicularly to the longitudinal groove 16. HF-voltage from an HF-voltage source 7 which can be connected to the proximal end of the hollow probe I can be applied to the cutting element 10 by way of connecting lines which for example are guided on or in the thrust rod. The other terminal of the HF-voltage source 7 is connected to a counterpart electrode which can be arranged for example on the hollow body 2—insulated in relation to the cutting element 10—or which can be applied as a separate electrode from the exterior to the area of tissue to be treated.

Figure 3:
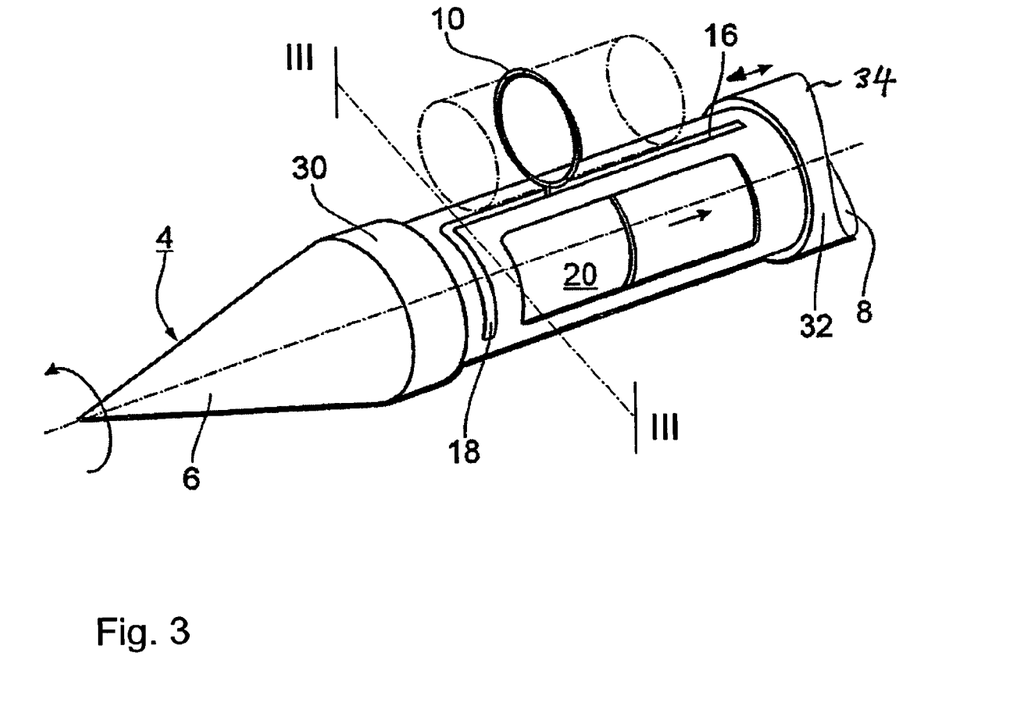
FIG. 3 is a perspective view of a second embodiment of the surgical hollow probe.
Figure 4:
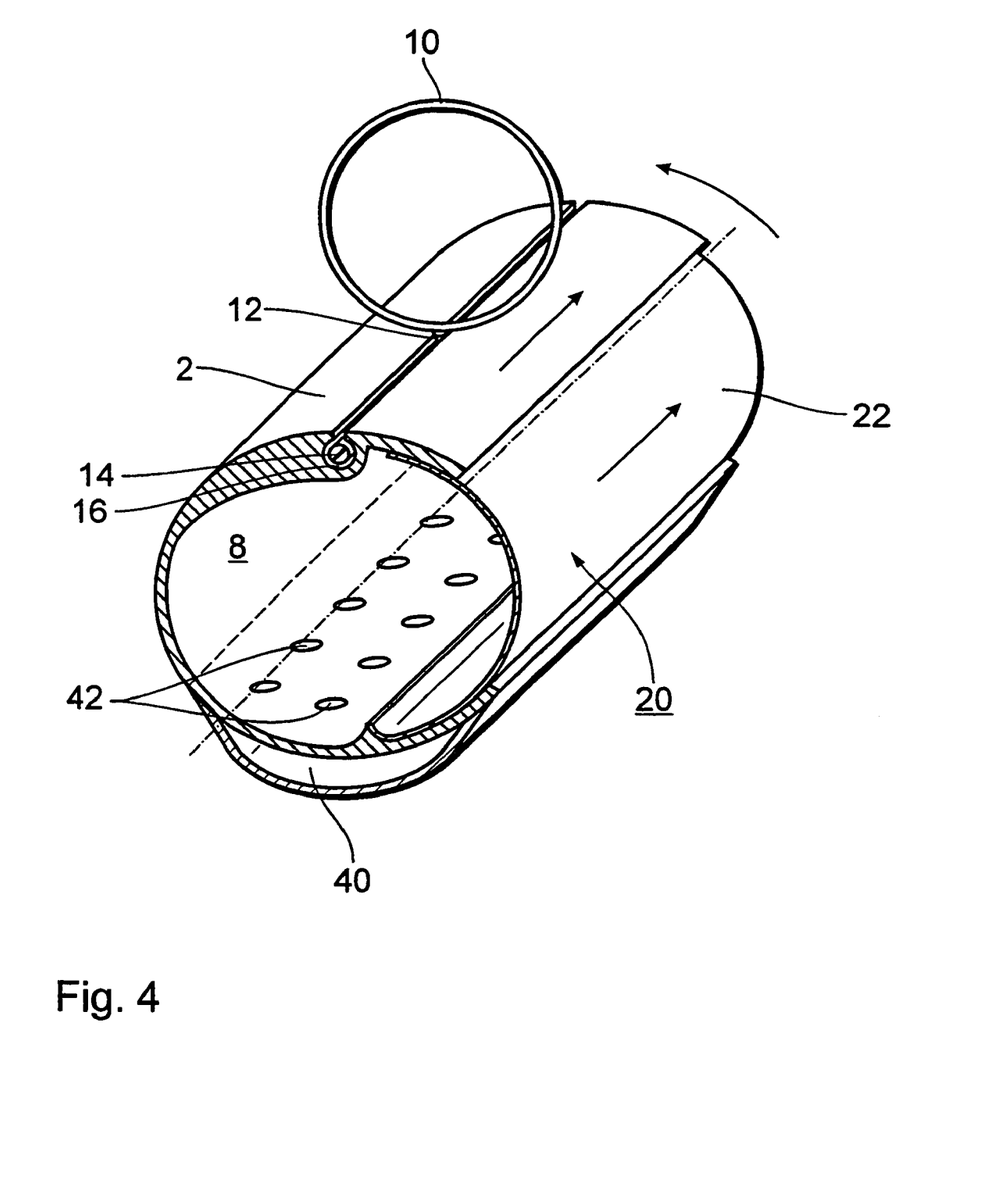
FIG. 4 is a view in cross-section taken along line III-III in FIG. 3.

The embodiment shown in FIGS. 3 and 4 substantially corresponds to the embodiment of FIGS. 1 and 2, with the same references denoting the same parts. In addition, however, in FIGS. 3 and 4 a first metal electrode 30 is applied to the distal end 6 of the hollow body 2. The electrode 30 covers the entire tip 6 and an adjoining axial portion of the hollow body 2. Arranged at a predetermined spacing from the first electrode 30, more specifically at the proximal end of the longitudinal groove 16 and the distal opening 20, is a second metal electrode 32 which is of a cylindrical shape. In addition, as is shown in particular in FIG. 4, the distal opening 20 is closable by means of an axially displaceable closure 22. Provided along the hollow body 2 is a suction air passage 40 which is in suction communication by way of suction openings 42 with the hollow passage 8 of the hollow body 2. The second electrode 32 is arranged directly on the hollow body 2 and is then at a fixed axial spacing from the first electrode 30. Alternatively, however, the second electrode 32 is disposed on a sleeve 34 which is supported slidably on the hollow body 2 so that, upon displacement of the sleeve 34, the axial spacing between the electrodes 30 and 32 is variable. The electrodes 30 and 32 are preferably cylindrical in shape and extend around the hollow body 2 and the sleeve 34 respectively at the outside periphery thereof.

Figure 5:
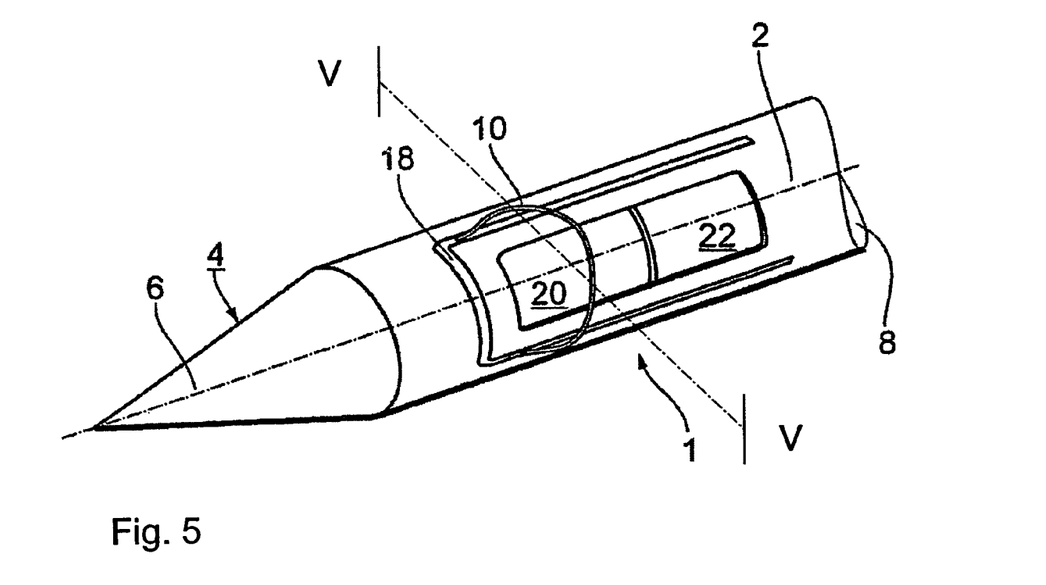
FIG. 5 is a perspective view of a third embodiment of the surgical hollow probe.
Figure 6:
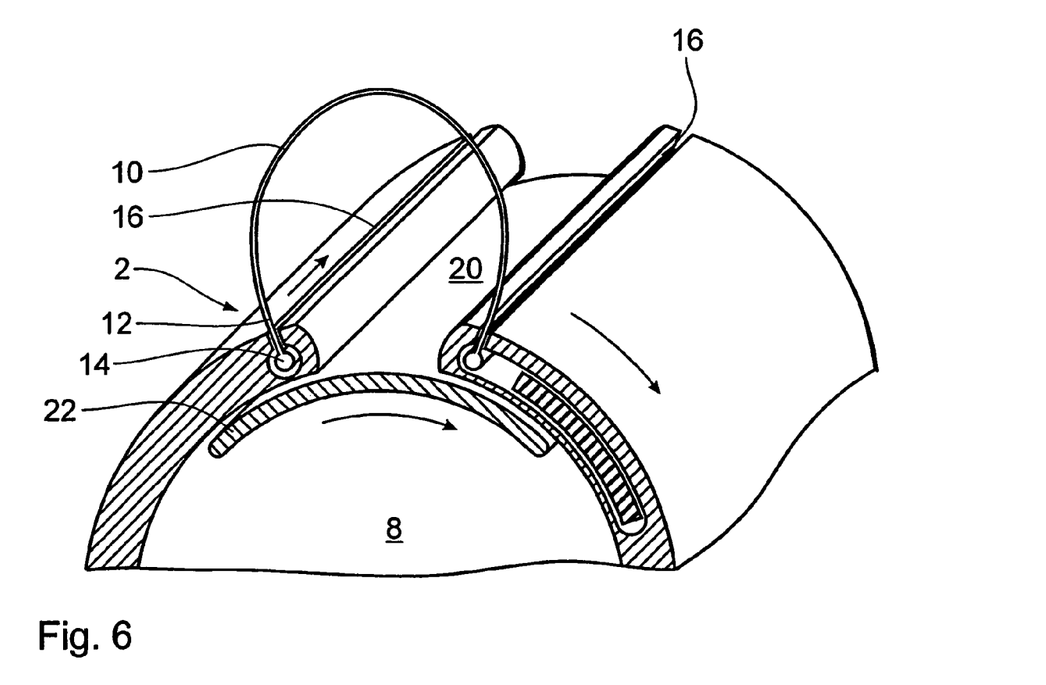
FIG. 6 is a view in cross-section taken along line V-V in FIG. 5, FIGS. 7 to 10 show various positions of the cutting element when carrying out a cutting Operation.

FIGS. 5 and 6 show a surgical hollow probe I which in terms of its basic elements corresponds to the embodiment shown in FIGS. 1 to 4 and which also has a circular-cylindrical hollow body 2 with a distal tip 6, a longitudinal axis 3 and a hollow passage 8. As an alternative to the embodiment shown in FIGS. 1 to 4, in FIGS. 5 and 6 the cutting element 10 is in the form of a wire loop whose two ends 12 are each secured to a respective thrust rod 14. The thrust rods 14 are supported slidably in parallel longitudinal grooves 16. Disposed between the two longitudinal grooves 16 is the distal opening 20 which is defined by wall edges extending parallel to the longitudinal grooves 16. The distal opening 20 is closable by a closure 22 which is supported displaceably in the peripheral direction on the inside surface of the hollow body 2. At their distal end, the two longitudinal grooves are connected by a slot 18 which extends perpendicularly to the longitudinal grooves 16 and the longitudinal axis 3, and which serves to provide that the cutting element 10 which can be formed from flexible wire, can be retracted into and extended from the hollow passage 8.

The cutting element 10, also referred to as a ring electrode, can either comprise a fixed, pre-shaped metal ring, for example consisting of high-quality steel, or it can comprise a flexible electrode material, for example a high-quality steel wire mesh, or a wire comprising an NiTi-alloy.

When the cutting element 10 is of a flexible nature, the cutting element can virtually fold together in the retracted condition within the hollow body 2. Further, the flexible cutting element 10 can be deployed when it is extended from the hollow body and in the deployed condition can be of a diameter which is larger than the diameter of the hollow body 2. When the flexible cutting element 10 is sufficiently elastic, the cutting element 10 can deploy of its own accord in the tissue to its original diameter, due to the prestressing effect in the material thereof. In that case, the cutting element 10 which is in the form of a ring or loop is secured at least one point in perpendicular relationship to a thrust rod 14 which can also be in the form of a thin tube and which in that way can accommodate in its interior the electrical feed line for the cutting element 10 which can be supplied with HF-voltage.

For the purposes of minimally invasive collection of tissue by means of the hollow probe I, the hollow probe I is firstly positioned by being inserted into the area of tissue in question. During the insertion procedure, until the tip of the probe reaches the target area, an HF-voltage is applied between the electrodes 30, 32 which extend cylindrically around the hollow body 2, or between one of those electrodes and an external counterpart electrode. The frequency and amplitude of that HF-voltage are such that the tissue which adjoins the hollow probe I experiences a local heating effect at between 55° and 100° C., preferably 600 and 80° C., for inactivation of cell metabolism, without in that case however destroying the cell and tissue matrix. That is effected after a predetermined time of between about 5 and 20 minutes, whereupon the supply of voltage to the two electrodes 30, 32 is terminated. That treatment causes pre-coagulation of the insertion passage and also of the target area, whereby the adjoining cells are inactivated and hardened so that mechanical spreading of any tumour cells is prevented. The cutting element 10 can then be extended from the hollow body 2 by way of an electromechanical actuating device until the cutting element is completely extended. In that case the surface formed by the cutting element 10 is perpendicular to the longitudinal axis 3 of the hollow body 2. At the time of extending the cutting element 10 into the tissue an HF-voltage is already being applied to the cutting element 10 and a counterpart electrode which is fitted on the hollow body 2 or applied from the exterior to the area of tissue in question. The cutting element 10 is then operated as an HF-cutting electrode.

Figure 7:
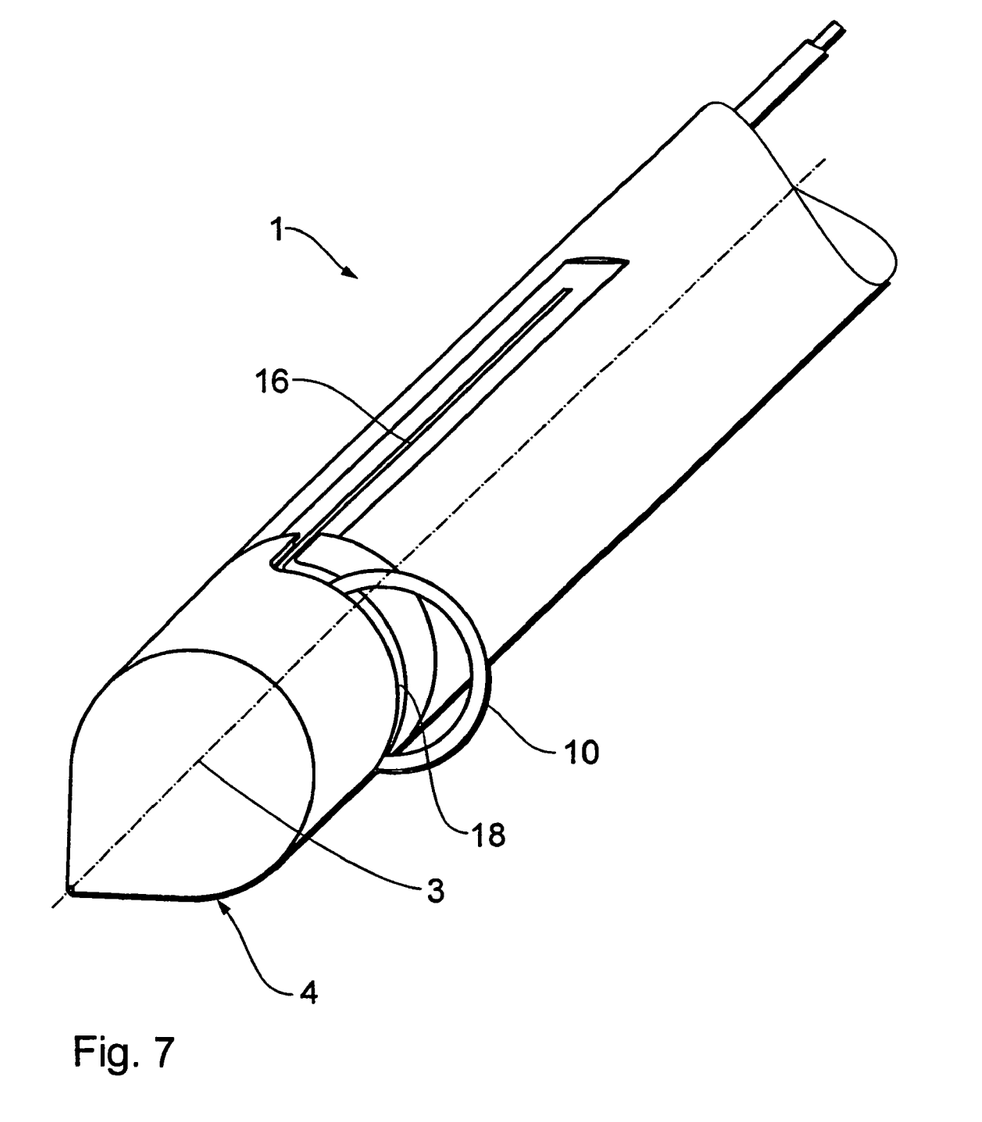
Figure 8:
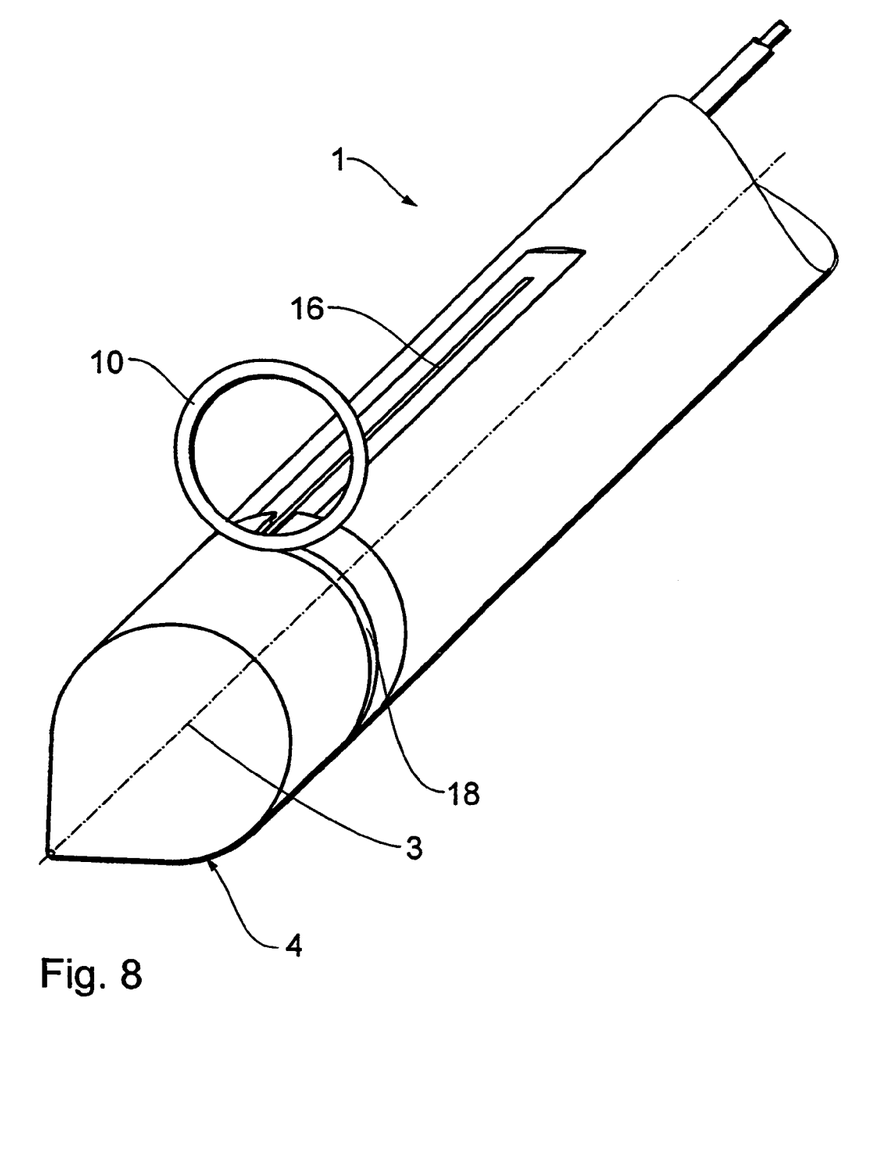
Figure 9:
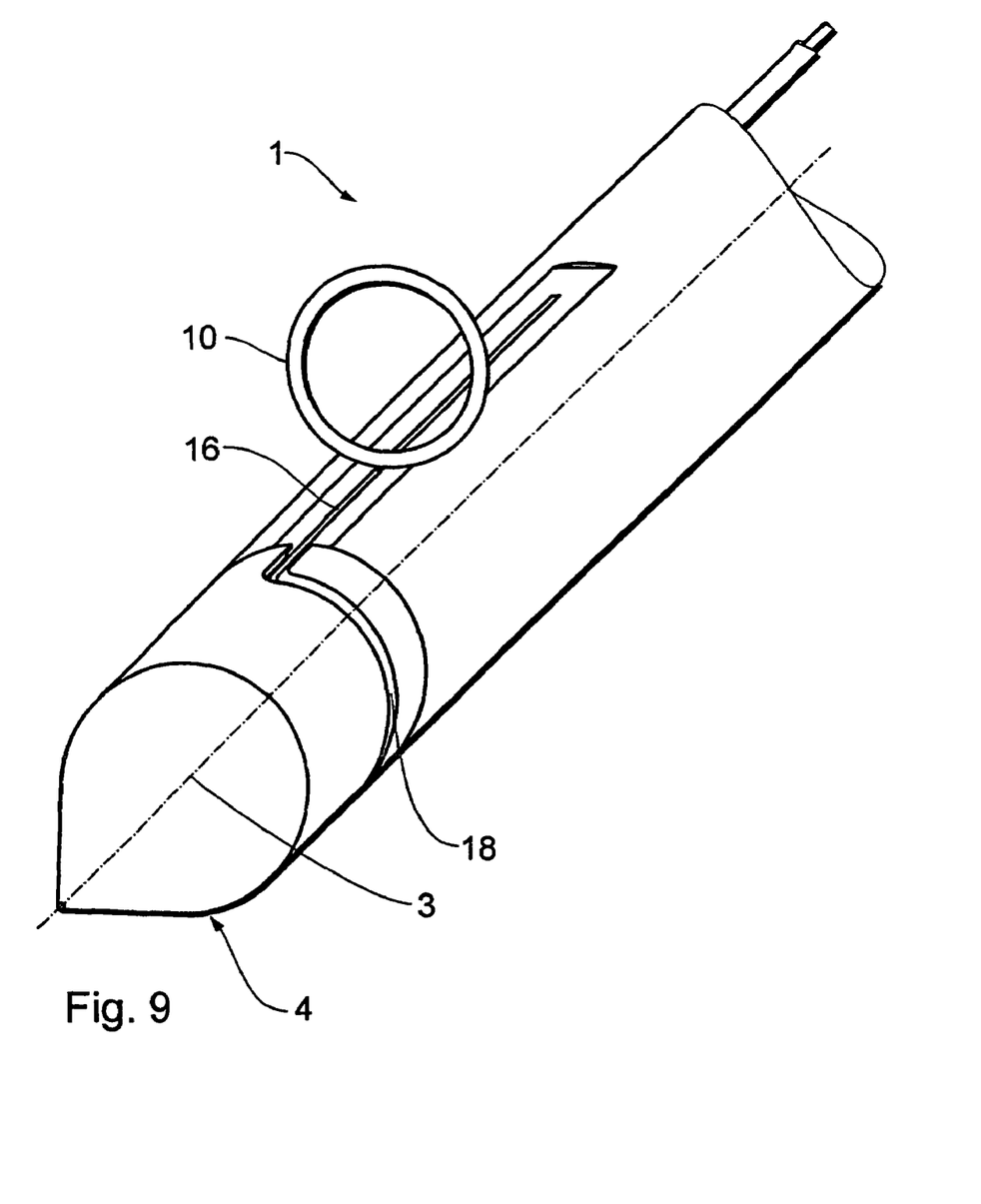
Figure 10:
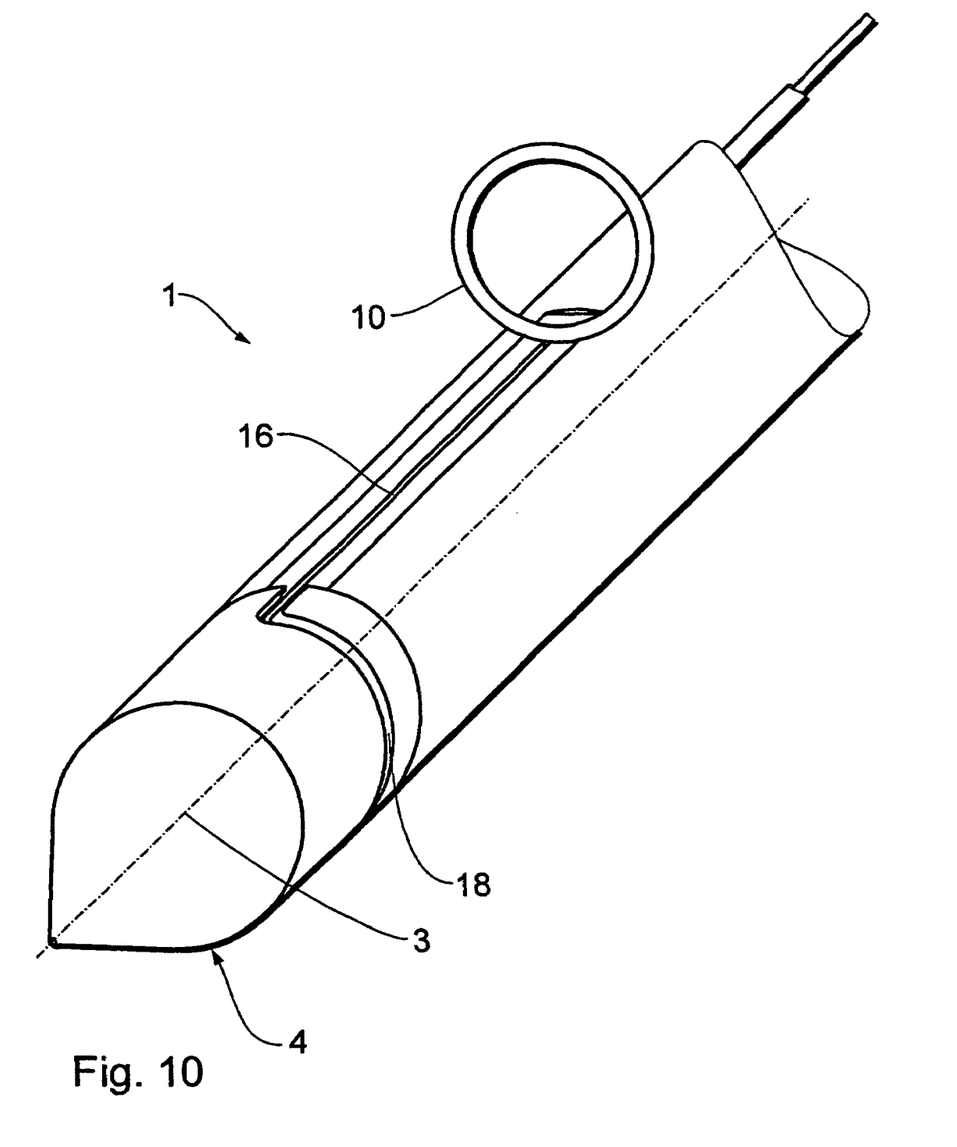

As can be seen in particular from FIGS. 7 to 10, the ring-shaped cutting element 10 can be extended outwardly from the hollow body 2 through the gap 18 by a rotary movement of the thrust rod 14, see FIGS. 7 and 8. The cutting element 10 can then be displaced by a translatory movement along the longitudinal groove 16, see FIGS. 9 and 10. If, during that cycle of movement, HF-voltage of a predetermined strength and at a predetermined frequency is applied to the cutting element 10, then the end face of a cylindrical core of tissue is cut out when the cutting element 10 is extended and the peripheral surface of the cylindrical core of tissue is then cut out in the longitudinal displacement of the cutting element. If then, with the cutting element 10 in the extended condition, the probe is rotated about its longitudinal axis 3, the cylindrical core of tissue is thereby also severed at its other end face because, in the rotary movement of the hollow probe I, the cutting element 10 is necessarily also rotated. When that movement takes place, the distal opening 20 which is still closed by the closure 22 is displaced into a position under the cylindrical core of tissue which has now been completely cut out. After opening of the closure 22, the cut-out cylindrical core of tissue can be passed through the distal opening 20 whose size is adapted to the geometry of the piece of tissue which has been cut out, by means of a vacuum flow into the hollow passage 8 and through the hollow passage 8, and can be removed by the user at the proximal end of the hollow probe 1.

Even relatively large cylindrical cores of tissue can be transferred through the distal opening 20 by virtue of the elastic characteristics of biological tissue. The cutting process for collecting a further cylindrical core of tissue can then be continued.

The probe 1 may include a mechanical device for transferring the cutout tissue into the distal opening 20 and for transporting the tissue through the hollow body 2 to the proximal opening of the hollow probe.

Figure 11:
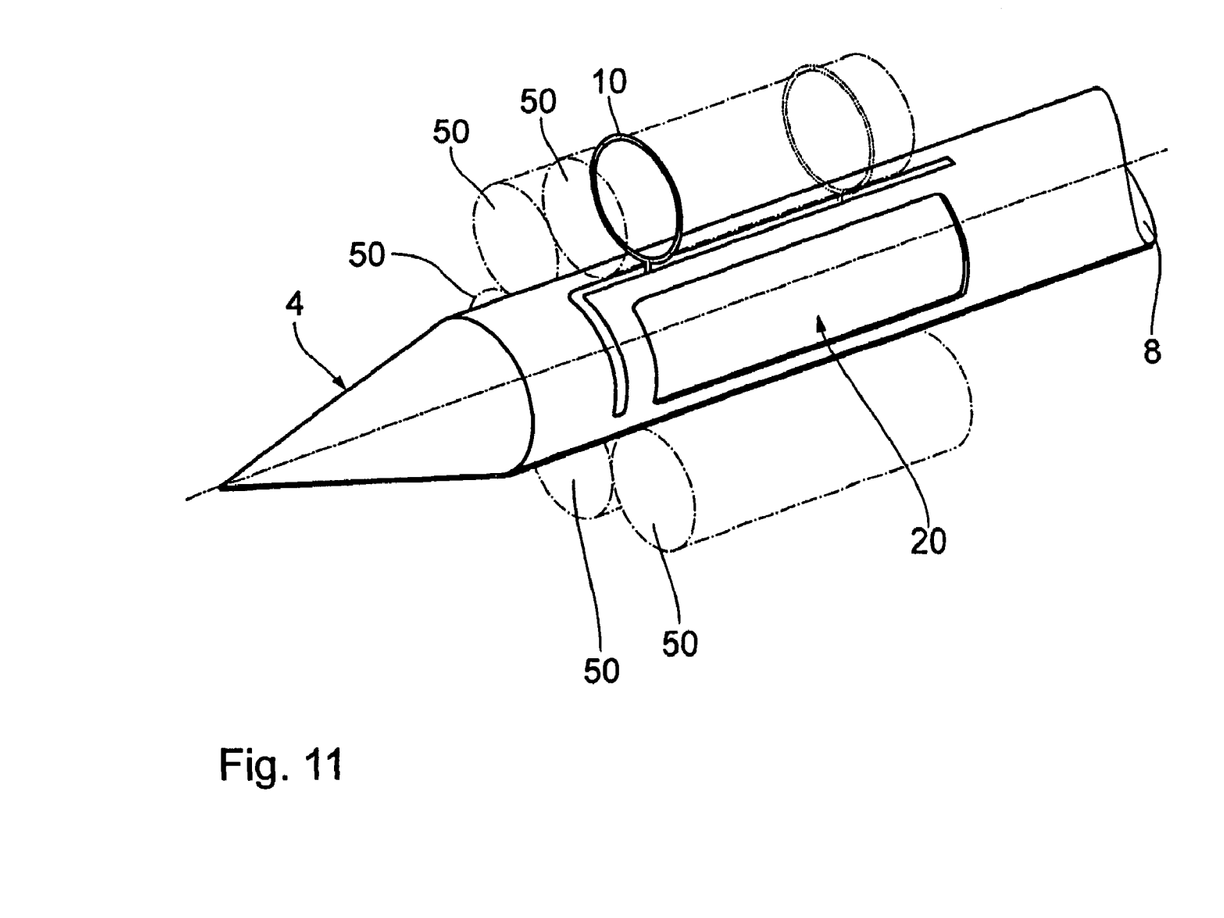
FIG. 11 is a diagrammatic view of the mode of Operation of the hollow probe as shown in FIGS. 1 to 10.

After electromechanical activation, the ring-shaped cutting element 10 is pushed to the distal tip 6 again and, in that movement, because of the applied HF-ac voltage, cuts out in blood-free manner a further cylinder of tissue 50 which—like the first cylinder 50 of tissue—extends outside the hollow probe in parallel relationship with the longitudinal axis 3 thereof. By again further rotating the hollow probe about its longitudinal axis 3 through a defined angular distance, the distal end face of the cylinder 50 of tissue is severed by the cutting element 10, and the distal opening 20 is again pushed into a position under the cylindrical core of tissue 50 which has been cut out and which can be transferred through that opening 20 to the user. In that way, by successive rotation about the longitudinal axis 3 and a respective longitudinal displacement of the cutting element 10 between each two successive rotational Steps, the cylindrical cores of tissue 50 which are disposed around the hollow probe I in adjacent relationship can be successively precisely electrosurgically incised and removed. Those tissue samples can then be used for pathological tissue investigation (histology). This procedure can be repeated until the starting position is again attained, after a rotary movement of the hollow probe I through 360°, see FIG. 11. Accordingly, in this manner, the user collects a volume of tissue which corresponds to a multiple of the diameter of the hollow probe 1.

The fact that HF-ac voltage is applied to the cutting element 10 during the cutting operation provides for virtually blood-free cutting of tissue without mechanical stresses, whereby styptic Intervention procedures which are required when using purely mechanical cutting processes are reduced. The risk of spreading tumour cells is also reduced to a minimum.

The mode of operation of the hollow probe I shown in FIGS. 5 and 6 is entirely similar to the mode of operation as was described for the embodiment shown in FIGS. 1 to 4, but in this case there is no need to reverse a rotary movement of the hollow probe I about its longitudinal axis 3 for severing the respective cylindrical core of tissue. The procedure is always such that to implement a cut at the end face, the cutting element 10 is extended from the hollow probe I, then the cutting element 10 is longitudinally displaced and then the cutting element 10 is retracted into the hollow probe I again, to produce the cut at the other end face of the cylindrical core of tissue. As the distal opening 20 is immediately below the tissue cells which have been cut out, the closure 22 is opened and the cylindrical core of tissue is transported away through the opening 20. It is only for the purposes of cutting out an adjacent cylindrical core of tissue that the probe is then rotated and the cutting element 10 is extended from the hollow probe again, and so forth.

The invention claimed is:

1. A surgical hollow probe for minimally invasive tissue removal, comprising:
    an elongate hollow body,
    a distal opening in the region of the distal end of the hollow body for receiving tissue, and
    an electrically conductive ring-shaped or loop-shaped cutting element is adapted to be extended from the hollow body and is adapted to be applied to an HF-voltage source, for electrosurgically cutting out tissue in the area around the distal opening of the hollow body,
    characterised in that the cutting element is adapted to be extended from or pivoted out of the hollow body transversely with respect to the longitudinal axis of the hollow body and is then displaceable outside the hollow body along the hollow body; and characterized in that the cutting element is in the form of a wire loop whose both ends are secured to two separate guide elements which are guided slidably at the outside surface of the hollow body in longitudinal grooves parallel to the longitudinal axis of the hollow body.

2. A surgical hollow probe according to claim 1 characterized in that the distal opening is provided in a peripheral wall of the hollow body between the longitudinal grooves.

3. A surgical hollow probe according to claim 1 characterized in that the distal opening of the hollow body is adjacent to one of the longitudinal grooves.

4. A surgical hollow probe according to claim 1 characterized in that the guide elements are in the form of thrust rods which extend from the distal end to the proximal end of the hollow body and which are supported slidably and rotatably in the longitudinal grooves.

5. A surgical hollow probe for minimally invasive tissue removal, comprising:
    an elongate hollow body,
    a distal opening in the region of the distal end of the hollow body for receiving tissue, and
    an electrically conductive ring-shaped or loop-shaped cutting element is adapted to be extended from the hollow body and is adapted to be applied to an HF-voltage source, for electrosurgically cutting out tissue in the area around the distal opening of the hollow body,
    characterised in that the cutting element is adapted to be extended from or pivoted out of the hollow body transversely with respect to the longitudinal axis of the hollow body and is then displaceable outside the hollow body along the hollow body;
    and characterized in that provided at least one of the distal or proximal ends of the displacement travel, in the peripheral wall of the hollow body is a gap through which the cutting element is adapted to extend from and retract into the hollow body.

6. A surgical hollow probe for minimally invasive tissue removal, comprising
    an elongate hollow body, having a distal end region and a proximal end region,
    a distal opening in the region of the distal end of the hollow body for receiving tissue, and
    an electrically conductive ring-shaped or loop-shaped cutting element is adapted to be extended from the hollow body and is adapted to be applied to an HF-voltage source, for electrosurgically cutting out tissue in the area around the distal opening of the hollow body, characterised in that the cutting element is adapted to be extended from or pivoted out of the hollow body transversely with respect to the longitudinal axis of the hollow body and is then displaceable outside the hollow body along the hollow body; and characterised by a suction removal device which is adapted to be connected to the proximal end of the hollow probe for sucking the cut-out tissue into the distal opening and for sucking the tissue away through the hollow passage of the hollow body to a proximal opening in the region of the proximal end of the hollow probe; and characterized in that the hollow body includes a separate suction air passage which extends from the connection of the suction removal device in the longitudinal direction to the distal opening and which is in suction communication over an entire length thereof with the hollow passage of the hollow body by way of suction openings.

7. A surgical hollow probe for minimally invasive tissue removal, comprising:
an elongate hollow body,
a distal opening in the region of the distal end of the hollow body for receiving tissue, and
an electrically conductive ring-shaped or loop-shaped cutting element is adapted to be extended from the hollow body and is adapted to be applied to an HF-voltage source, for electrosurgically cutting out tissue in the area around the distal opening of the hollow body,
characterized in that the cutting element is adapted to be pivoted out of the hollow body transversely with respect to the longitudinal axis of the hollow body and is then displaceable outside the hollow body along the hollow body; and characterized in that the cutting element is slidably guided on the hollow body in parallel to the longitudinal axis of the hollow body; and
characterized in that the distal end of the hollow probe converges to a point.

8. A surgical hollow probe for minimally invasive tissue removal, comprising:
an elongate hollow body,
a distal opening in the region of the distal end of the hollow body for receiving tissue, and
an electrically conductive ring-shaped or loop-shaped cutting element is adapted to be extended from the hollow body and is adapted to be applied to an HF-voltage source, for electrosurgically cutting out tissue in the area around the distal opening of the hollow body,
characterized in that the cutting element is adapted to be extended from or pivoted out of the hollow body transversely with respect to the longitudinal axis of the hollow body and is then displaceable outside the hollow body along the hollow body; and
characterized in that an electrode is arranged on a surface of the hollow body in the region of the distal end and characterized in that an HF-voltage source is adapted to be connected with one terminal to the electrode and with a second terminal to the cutting element, in order locally to limit the HF-current through the tissue.

9. A surgical hollow probe for minimally invasive tissue removal, comprising:
an elongate hollow body,
a distal opening in the region of the distal end of the hollow body for receiving tissue, and
an electrically conductive ring-shaped or loop-shaped cutting element is adapted to be extended from the hollow body and is adapted to be applied to an HF-voltage source, for electrosurgically cutting out tissue in the area around the distal opening of the hollow body,
characterized in that the cutting element is adapted to be extended from or pivoted out of the hollow body transversely with respect to the longitudinal axis of the hollow body and is then displaceable outside the hollow body along the hollow body; and
characterized in that arranged on a surface of the hollow body in the region of the distal end are a first electrode and at an axial spacing a second electrode, to which HF-voltage is adapted to be applied in order to heat adjoining tissue upon insertion of the probe.

10. A surgical hollow probe according to claim 9 characterized in that the first electrode and the second electrode are of a cylindrical shape around the longitudinal axis.

11. A surgical hollow probe according to claim 9 characterized in that at least one of the first and second electrodes are axially displaceable.

12. A surgical hollow probe according to claim 9, characterized in that the second electrode is arranged on a sleeve which is axially displaceable on the hollow body.

13. A surgical hollow probe according to claim 9 characterized in that at least one of the first electrode and the second electrode serves as a counterpart electrode for the cutting element.

14. A surgical hollow probe for minimally invasive tissue removal, comprising:
an elongate hollow body,
a distal opening in the region of the distal end of the hollow body for receiving tissue, and
an electrically conductive ring-shaped or loop-shaped cutting element is adapted to be pivoted out from the hollow body transversely therefrom and is adapted to be applied to an HF-voltage source, for electrosurgically cutting out tissue in the area around the distal opening of the hollow body,
characterised in that the cutting element is adapted to be extended from or pivoted out of the hollow body transversely with respect to the longitudinal axis of the hollow body and is then displaceable outside the hollow body along the hollow body; and
characterised in that the cutting element is slidably guided on the hollow body in parallel to the longitudinal axis of the hollow body; and
characterised in that the cutting element is in the form of a wire loop whose both ends are secured to a common guide element which is guided slidably at the outside surface of the hollow body in a longitudinal groove parallel to the longitudinal axis of the hollow body.

15. A surgical hollow probe according to claim 14 characterised in that the distal opening of the hollow body is adjacent to the longitudinal groove.

16. A surgical hollow probe according to claim 14, characterized in that the guide elements are in the form of a thrust rod which extends from the distal end to the proximal end of the hollow body and which is supported slidably and rotatably in the longitudinal groove.

* * * * *